(12) United States Patent
Lindegger (10) Patent No.: US 9,377,513 B2
(45) Date of Patent: Jun. 28, 2016

(54) AMBULATORY INFUSION DEVICE WITH REPLACEABLE ENERGY STORAGE AND METHOD OF MONITORING THE ENERGY STORAGE

(71) Applicant: Roche Diagnostics International AG, Rotkreuz (CH)

(72) Inventor: Stefan Lindegger, Huttwil (CH)

(73) Assignee: Roche Diagnostics International AG, Rotkreuz (CH)

(*) Notice: Subject to any disclaimer, the term of this patent is extended or adjusted under 35 U.S.C. 154(b) by 531 days.

(21) Appl. No.: 13/761,215

(22) Filed: Feb. 7, 2013

(65) Prior Publication Data

US 2013/0147490 A1  Jun. 13, 2013

Related U.S. Application Data

(63) Continuation of application No. PCT/EP2011/061534, filed on Jul. 7, 2011.

(30) Foreign Application Priority Data

Aug. 18, 2010 (EP) .................................. 10173316

(51) Int. Cl.
| | | |
|---|---|---|
| *G01N 27/416* | (2006.01) | |
| *A61M 37/00* | (2006.01) | |
| *A61M 5/20* | (2006.01) | |
| *G01R 31/36* | (2006.01) | |
| *A61M 5/14* | (2006.01) | |

(Continued)

(52) U.S. Cl.
CPC ............... *G01R 31/362* (2013.01); *A61M 5/14* (2013.01); *A61M 5/1413* (2013.01); *A61M 5/14244* (2013.01); *A61M 5/16831* (2013.01); *A61M 5/172* (2013.01)

(58) Field of Classification Search
CPC ............... Y02E 60/12; G01R 31/3682; G01R 31/3686; H01M 6/505; H01M 10/488
USPC .................................. 324/435; 604/131–139
See application file for complete search history.

(56) References Cited

U.S. PATENT DOCUMENTS

| 4,488,555 A | 12/1984 | Imran | |
|---|---|---|---|
| 5,115,182 A * | 5/1992 | Ehmke et al. | .................. 320/136 |

(Continued)

FOREIGN PATENT DOCUMENTS

| EP | 1072285 A1 | 1/2001 |
|---|---|---|
| GB | 2312049 A | 10/1997 |

(Continued)

*Primary Examiner* — Richard Isla Rodas
*Assistant Examiner* — Mohammed J Sharief
(74) *Attorney, Agent, or Firm* — Roche Diagnostics International AG (57) ABSTRACT

An ambulatory infusion device comprising a replaceable energy storage for electrically powering its functional units is presented. Control units provide to a monitoring system data about energy consuming activities or consumed energy by the functional units. Based on this data, the monitoring system determines energy consumed by the functional units and triggers measurement of the voltage of the energy storage at a point in time which depends on the determined energy consumed in a time interval preceding the point in time. Adapting the time of measurement to the actual energy drawn from the energy storage makes it possible to detect reliably and early a low energy state of any conventional standard battery, regardless of its electrochemical design and electrical behavior.

15 Claims, 4 Drawing Sheets

(51) Int. Cl.
  *A61M 5/142* (2006.01)
  *A61M 5/168* (2006.01)
  *A61M 5/172* (2006.01)

(56) References Cited

U.S. PATENT DOCUMENTS

| 5,321,392 | A | 6/1994 | Skakoon et al. |
| 7,469,161 | B1 | 12/2008 | Gandhi et al. |
| 2004/0199146 | A1* | 10/2004 | Rogers ............ A61M 5/14276 604/891.1 |
| 2004/0251875 | A1 | 12/2004 | Kinoshita et al. |
| 2009/0069749 | A1 | 3/2009 | Miller et al. |
| 2009/0146826 | A1 | 6/2009 | Gofman et al. |
| 2010/0298686 | A1* | 11/2010 | Reggiardo ............ A61B 5/0002 600/365 |

FOREIGN PATENT DOCUMENTS

| WO | 2006/048838 A1 | 5/2006 |
| WO | 2011/005152 A1 | 1/2011 |

* cited by examiner

AMBULATORY INFUSION DEVICE WITH REPLACEABLE ENERGY STORAGE AND METHOD OF MONITORING THE ENERGY STORAGE

CROSS-REFERENCE TO RELATED APPLICATIONS

This application is a continuation of PCT/EP2011/061534, filed Jul. 7, 2011, which is based on and claims priority to EP 10173316.0, filed Aug. 18, 2010, which is hereby incorporated by reference.

BACKGROUND

The present disclosure generally relates to relates to an ambulatory infusion device comprising a replaceable energy storage and a method of monitoring a replaceable energy storage of a medical device and, in particular, to an ambulatory infusion device which comprises a replaceable energy storage for electrically powering several functional units of the device and a measuring module configured to measure the voltage of the energy storage.

Medical devices are required to comply with strict requirements concerning availability and reliable power supply. Specifically, for medical devices such as external ambulatory infusion devices, regulatory requirements demand secure monitoring of energy cells that are used to power the device and signaling in good time to the user when the energy cell is expected to be depleted.

External ambulatory infusion devices for the infusion of a liquid drug over an extended time period are known in the art for a number of therapies. In particular, such devices form the basis for a state-of-the-art therapy of Diabetes Mellitus by CSII (Continuous Subcutaneous Insulin Infusion). Besides diabetes therapy, these devices may be used for a number of further therapies, such as cancer treatment or pain therapy, without requiring substantial modification.

Typically, these devices are powered by user-replaceable energy storage, particularly, by one or more energy cells including rechargeable and non-rechargeable batteries. For the batteries, distinct performance characteristics are generally required for safe and reliable operation. Therefore, some devices are powered by special-purpose power packs which are especially designed to meet device requirements. This approach, however, is accompanied by some drawbacks. In particular, the user has to stock the power packs and carry a number of them, for example when traveling. In addition, the price of the power packs is high because of the comparatively low production volumes.

Some other devices are therefore designed to be powered by widely available, conventional batteries, such as AA or AAA cells. Such standard batteries have no proprietary and/or device-specific features or built-in energy/charge-monitoring systems. Consequently, in order to adhere to regulatory requirements, such medical devices must be configured to monitor the energy/charge of such standard batteries. Accordingly, state-of-the-art devices perform battery tests by connecting the battery terminals periodically to a given test load, for stressing the battery with a defined stress test, and measuring the corresponding terminal voltage. An alert is generated when the measured voltage is below a given threshold voltage. The testing interval between consecutive tests is typically in the range of some minutes. However, standard batteries come in a variety of different electrochemical designs and electrical behavior, and thus a device may spontaneously terminate operation without alerting the user, when the battery's voltage drops, during operation of the device, from a high level at, which no alert would be generated, to a very low level, which is no longer sufficient for operating the device, with a steep drop of the terminal voltage and within and in a short time. Because in this case, the user is not aware of the terminated infusion of the drug or substance, this may result in severe adverse effects.

Therefore, there is a need for a device and method to monitor reliably the energy of the replaceable energy storage of an ambulatory infusion device.

SUMMARY

According to the present disclosure, a device and method for monitoring a replaceable energy storage of a medical device which includes several functional units electrically powered by the energy storage is presented. The device and method comprises determining on an ongoing basis energy, or charge, consumed by the functional units by adding up amounts of energy, or charge, based on data provided by control units associated with the functional units. A voltage of the energy storage is measured at a point in time determined based on the energy, or charge, consumed by the functional units in a time interval preceding the point in time. An alarm is generated depending on the voltage of the energy storage.

In accordance with one embodiment of the present disclosure, a computer program product comprising a computer readable medium having stored thereon computer program code configured to direct a processor of a medical device, which includes a replaceable energy storage for electrically powering several functional units of the medical device is presented.

Accordingly, it is a feature of the embodiments of the present disclosure to provide a device and method to monitor reliably the energy, or charge, of the replaceable energy storage of an ambulatory infusion device. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A medical device, such as, for example, an ambulatory infusion device, can comprise a replaceable energy storage for electrically powering several functional units of the medical device. A measuring module can measure a voltage of the energy storage that can be further provided with a monitoring system that can determine on an ongoing basis energy, or charge, consumed by the functional units by adding up amounts of energy based on data provided by control units associated with the functional units, can trigger the measuring module to measure the voltage of the energy storage at a point in time which can depend on the energy consumed by the functional units in a time interval preceding the point in time, and can generate an alarm depending on the voltage of the energy storage. In one embodiment, the beginning and the end of the time interval can be defined by consecutive voltage measurements, i.e. the time interval can be in between two voltage measurements.

The monitoring system can make it possible to determine on an ongoing basis the energy consumed by the functional units, and to determine a point in time for measuring the voltage of the energy storage based on counting the energy consumed by the functional units in a time interval preceding the point in time. Thus, it can be possible to detect reliably and early a low energy state of any conventional standard and/or rechargeable battery regardless of its electrochemical design and electrical behavior, because the time of measurement is adapted dynamically to the actual energy or charge drawn from the battery.

As stated above, the energy consumed by the functional units can be determined and the point in time for measuring the voltage of the energy storage can be determined depending on the consumed energy, respectively. Nevertheless, from a practical point of view, it can be favorable to determine the charge consumed by the functional units and to determine the point in time for measuring the voltage depending on the consumed charge, because the current that is drawn by the individual functional units can typically be known or can be easily determined, and the capacity of batteries can be also given in mAh, i.e. as a measure of charge. If the consumed charge is counted for a number of functional units, all of them can be operated at the same voltage or their individual supply voltages can be computationally converted to a deemed common voltage, for example the nominal voltage of the energy storage or the supply voltage of a processor. The energy that is stored by the energy storage can be approximately its capacity in mAh multiplied with its nominal voltage. For a given power consumption of a functional unit, a respective current can be drawn. For determining the consumed energy rather than the consumed charge or drawn current, respectively, the consumed energy of the different functional units can be summed up directly, independent and regardless of possible differences in their supply voltages. However, for the purposes of this disclosure, it can be understood that the terms energy and charge can be used interchangeable without deviating from the scope of the disclosure.

In one embodiment, the functional units comprise in each case at least one functional hardware unit controlled by a control unit can provide to the monitoring system data about energy consuming activities, or energy consumed by the hardware unit, and the monitoring system can determine the energy consumed by the functional units based on the data provided by the control units controlling the hardware units. Thus, the control units can make it possible to assess the energy drawn from the energy storage, without having to put a stress load on the energy storage. The control units can merely provide to the monitoring system data about energy consuming activities performed by the hardware units, or energy consumed by the hardware units, thereby enabling the monitoring system to add up amounts of energy, responsive and corresponding to the data provided by the control units, such as to calculate the total energy consumed by the functional units.

In another embodiment, the monitoring system can compare a current value of energy consumed by the functional units to an energy threshold value, can trigger the measuring module to measure the voltage of the energy storage for cases where the current value of consumed energy exceeds the energy threshold value, and can reset the current value of energy consumed by the energy threshold value, upon having triggered the measuring module.

In some embodiments, the monitoring system can determine the energy threshold value depending on the type of energy storage used in the device, such as, for example, the type of battery, the current temperature value, the course or gradient of the temperature value, the voltage of the energy storage, and/or the course or gradient of the voltage of the energy storage and the like. Accordingly, the accuracy of monitoring the battery's energy state can further be improved by taking into consideration individual characteristics of different types of batteries and the influence of different and/or varying temperature.

In one embodiment, the monitoring system can generate a preliminary alarm indicative of a low energy level, sufficient for supporting further operation of the device, for cases where the voltage of the energy storage meets alarm conditions associated with an upper voltage threshold value, and can generate an end alarm indicative of a low energy level, insufficient for supporting further operation of the device, for cases where the voltage of the energy storage meets alarm conditions associated with a lower voltage threshold value.

In another embodiment, the monitoring system can maintain counters for several voltage threshold values, can increment a counter value when the voltage of the energy storage falls below the respective voltage threshold value and can decrement the counter value when the energy storage subsequently exceeds the respective voltage threshold value again, up to a defined counter threshold value when the energy storage is considered to have fallen definitely below the respective voltage threshold value. Accordingly, the accuracy of monitoring the battery's energy state can further be improved by taking into consideration fluctuation of the battery's power capacity caused, for example, by a variation in temperature.

In yet another embodiment, the monitoring system can maintain an event log including for the voltage threshold values in each case a point in time when the energy storage has fallen definitely below the respective voltage threshold value. Thus, the temporal discharge behavior of different types of batteries can be recorded over an extended voltage range, making possible statistical evaluation of different types of batteries and/or further refinement of battery monitoring based on individual discharge characteristics of different types of batteries.

In addition to a medical device, such as an ambulatory infusion device, a method of monitoring a replaceable energy storage of the medical device and a computer program product comprising a computer readable medium having stored thereon computer program code configured to direct a processor of the medical device are presented. The computer program code can direct the processor such that the medical device can determine on an ongoing basis energy consumed by the functional units, can trigger a measuring module of the device to measure the voltage of the energy storage at a point in time determined based on the energy consumed by the functional units in a time interval preceding the point in time, and can generate an alarm depending on the voltage of the energy storage.

Figure 1:
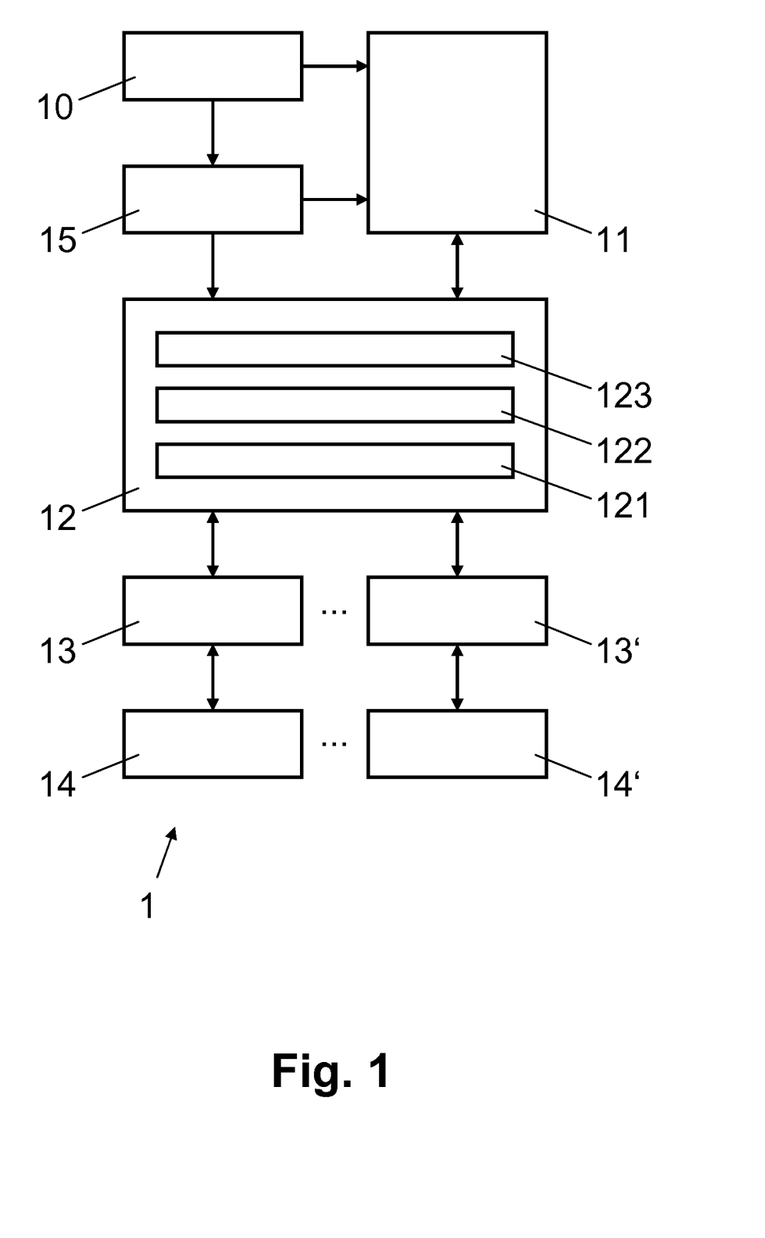
FIG. 1 illustrates a block diagram illustrating schematically a medical device with a replaceable energy storage and a monitoring system for monitoring the energy storage according to an embodiment of the present disclosure.
Figure 2:
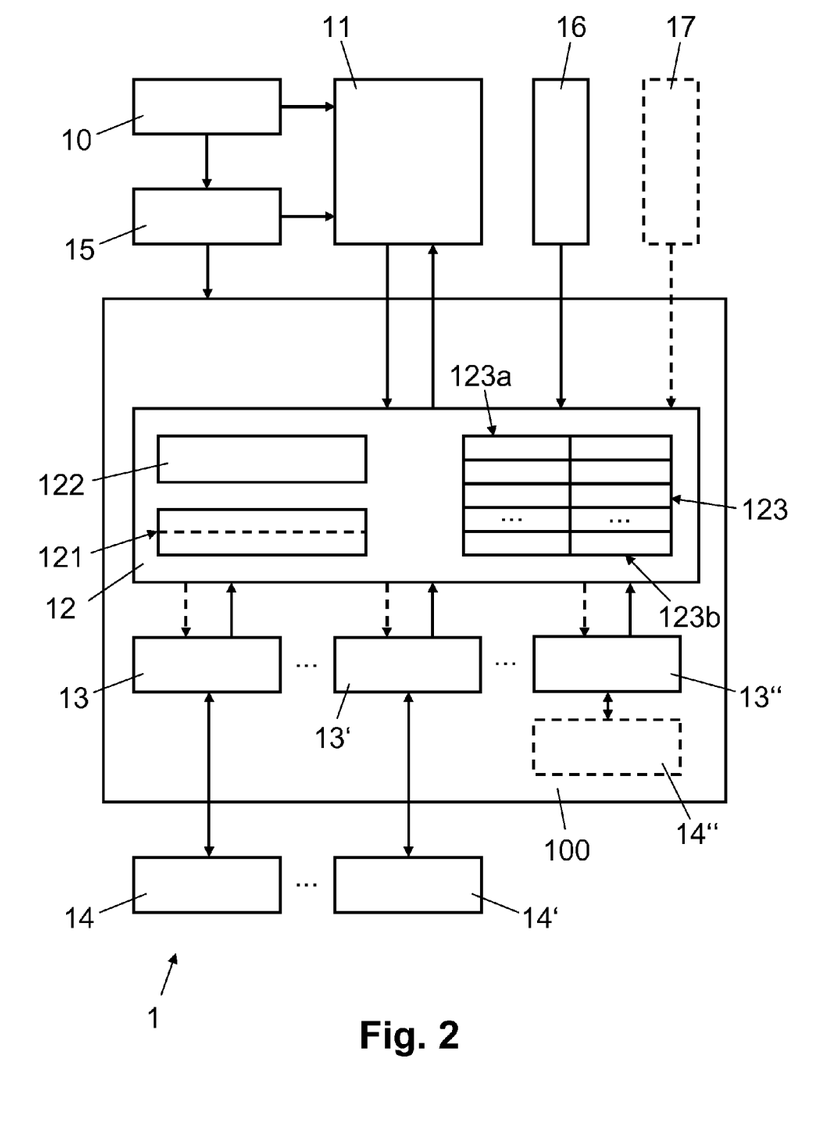
FIG. 2 illustrates a block diagram illustrating schematically a medical device with a replaceable energy storage and a device control unit which includes a monitoring system for monitoring the energy storage according to an embodiment of the present disclosure.

Referring initially to FIGS. 1 and 2, reference numeral 1 can refer to a device, such as, a medical device such as, for example, an ambulatory infusion device. Device 1 can comprise several functional units 14, 14', 14", such as, functional hardware units such as a motor drive for insulin infusion (pump), a display, a vibrator, a loudspeaker, an illumination device, and the like. The functional units 14, 14', 14" can be electrically powered by a user-replaceable energy storage 10, such as, for example, one or more standard energy cells, i.e. a conventional disposable or rechargeable battery, such as an alkaline battery providing a voltage of U=~0.9V−~1.6V, a NiMh rechargeable battery providing a voltage of U=~0.9V−~1.4V, or a Lithium primary cell providing a voltage of U=~1.1V−~1.8V, without any proprietary and/or device-specific features or built-in energy/charge-monitoring system.

As illustrated in FIGS. 1 and 2, the functional units 14, 14', 14" can be each controlled by a control unit 13, 13', 13". For example, the control units 13, 13', 13" can control insulin infusion; visual display of information; processing of user data entries; generate acoustic, vibration, and visual alarms; and the like.

For communication and control purposes, the one or more processors, and thus the control units 13, 13', 13", can be connected to the functional units 14, 14', 14" by way of serial or parallel data buses, signaling lines, and/or power lines.

As illustrated in FIGS. 1 and 2, device 1 can further comprise a power supply module 15, a measuring module 11, and a monitoring system 12.

Optionally, the power supply module 15 can comprise an electronic circuit to generate the voltage supplied by the energy storage 10 the supply voltage(s) for consumers in the device 1, for example, the functional units 14, 14', 14" and the device control unit 100 including the control units 13, 13', 13" and the monitoring system 12. In different embodiments, some consumers, for example, some of the functional units 14, 14', 14", can be directly connected to the energy storage 10 while others can be connected via the electronic circuit of the power supply module 15.

The measuring module 11 can measure the voltage supplied by the energy storage 10. Specifically, the measuring module 11 can measure the voltage or charge of the energy storage 10 upon request by the monitoring system 12. The measuring module 11 can perform the measurement by loading the energy storage 10 according to a defined load profile L, starting at a point in time Tm, and measuring the current value of the voltage or charge of the energy storage 10, at a defined point in time Tu of the load profile L. The load profile L can comprise one or more Ohm resistive loads L1, L2, L3 which can be connected to the energy storage 10, either directly or through the measuring module 11, for defined period of times T1, T2, T3.

Figure 3:
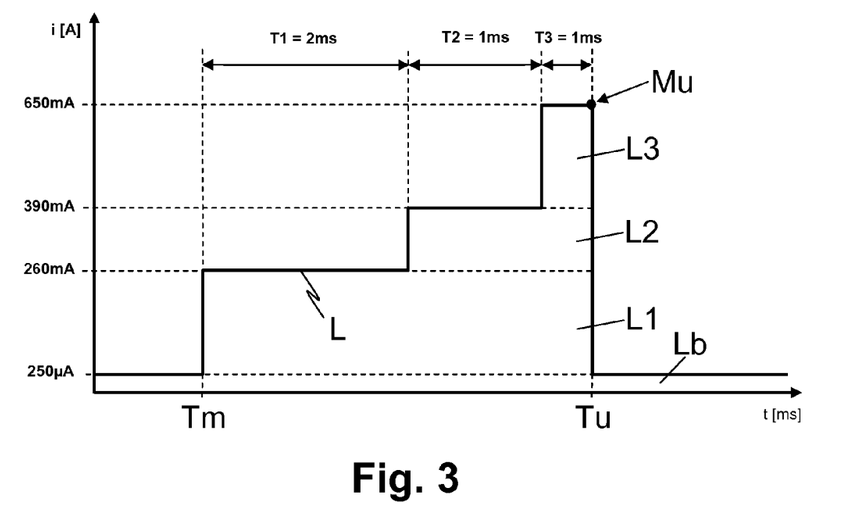
FIG. 3 illustrates a graph illustrating an example of a load profile for measuring the supply voltage of an energy storage according to an embodiment of the present disclosure.

FIG. 3 illustrates an example of a load profile L comprising a base load Lb representative of the basic power requirement of the device 1 and drawing a base current of i=μ250A; a first load L1 added to the base load Lb and drawing an increased current of i=260 mA for a defined time period of e.g. T1=2 ms; a second load L2 added to the base load Lb and the first load L1 and drawing a further increased current of i=390 mA for an additional time period of e.g. T2=1 ms; and a third load L3 added to the base load Lb, the first load L1, and the second load L2, and drawing a maximum load current of i=650 mA for an additional time period of e.g. T3=1 ms. The current value of the voltage of the energy storage 10 can be measured at a defined measurement point Mu of the load profile L at a corresponding point in time Tu. At the measurement point Mu/Tu, the current voltage of the energy storage 10 can be supplied to the monitoring system 12 or device control unit 100, respectively. Depending on the embodiment, the current voltage can be supplied via an interface as an analogue value for A/D conversion by the device control unit 100, or as a digital data value provided by an A/D converter of the measuring module 11.

As illustrated schematically in FIGS. 1 and 2, the monitoring system 12 can comprise or can have access to a data store including one or more energy threshold values 121, a data store including a current value of consumed energy 122, and a data store including different voltage threshold values 123. As shown in FIG. 2, the individual voltage threshold values 123a can be each assigned to a counter 123b which will be described later in more detail.

In one embodiment, there can be one static voltage threshold value 121. However, the energy threshold values 121 can include an upper energy threshold value and a lower energy threshold value, can be selected depending on the voltage of the energy storage 10, as will be explained later in more detail.

In another embodiment, the energy threshold values 121 can be set dynamically by the monitoring system 12 depending on the type of energy storage 10 used in the device 1, the current temperature value as provided by the temperature sensor 17, the course or gradient of the temperature value provided by the temperature sensor 17 (for example, a lower energy threshold value for lower temperatures, and a higher energy or charge threshold value for higher temperature), the voltage of the energy storage 10, and/or the course or gradient of the voltage of the energy storage 10.

In an additional embodiment, further measurements of the voltage or charge of the energy storage 10 can be triggered depending on varying temperature, particularly for decreasing (cooler) temperature values. This can be advantageous because energy storages show reduced endurance and power rating with colder temperatures. For example, the temperature can be measured periodically and compared to the value of a trailing pointer. If the measured temperature value is higher than the value of the trailing pointer, the value of the trailing pointer can be set to the measured temperature value. Otherwise, if the temperature is lower than the value of the trailing pointer, the value of the trailing pointer may not be altered, unless the measured temperature is more than a defined threshold value, for example about 5° C., lower than the value of the trailing pointer, in which case the value of the trailing pointer can be set to the measured temperature value and a measurement of the voltage or charge of the energy storage 10 can be triggered. The results of these temperature dependent voltage measurements can be processed the same way as the energy dependent voltage measurements.

As illustrated in FIG. 2, the monitoring system 12 and the control units 13, 13', 13" can be arranged and implemented in device control unit 100 which can comprise one or more operable microprocessors with program and data memory. In one embodiment, the device control unit 100 can further comprise functional units 14" controlled by a control unit 13". The monitoring system 12 and the control units 13, 13', 13" can be implemented as programmed software modules comprising computer program code for controlling one or more processors of the device control unit 100 or device 1, respectively. The computer program code can be stored on a computer-readable medium connected fixed or removably to the one or more processors. One skilled in the art can understand, however, that in alternative embodiments, the monitoring system 12 and/or the control units 13, 13', 13" can be implemented fully or at least partly by way of hardware components.

As illustrated in FIG. 2, device 1 can further comprise a clock unit 16 which can provide to the monitoring system 12 or device control unit 100, respectively, a time base and can be part of, or external, to the device control unit 100. Furthermore, in one embodiment, device 1 can comprise a temperature sensor 17 which can be part of or external to the device control unit 100, and can be connected to the monitoring system 12 or device control unit 100, respectively.

Figure 4:
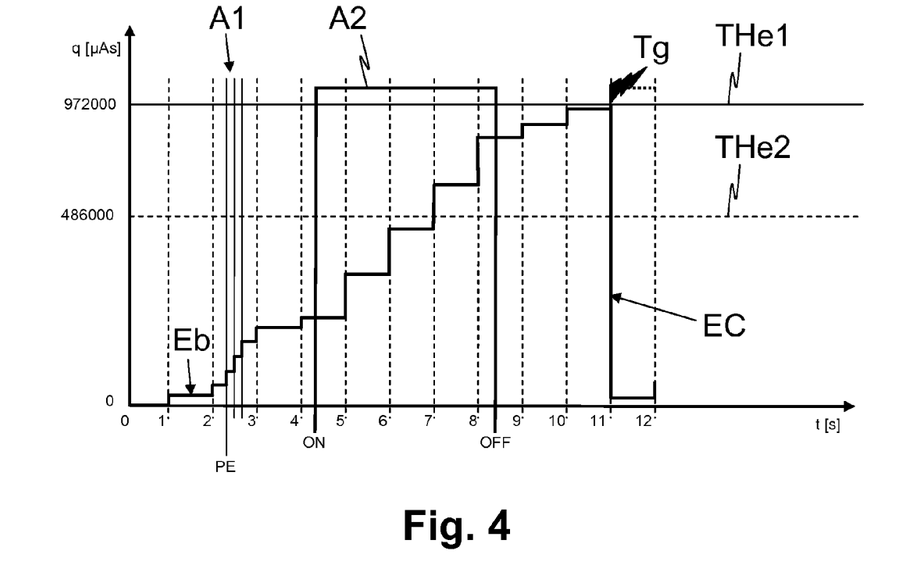
FIG. 4 illustrates a graph illustrating an example of determining energy consumption based on activities performed by functional units of the medical device according to an embodiment of the present disclosure.
Figure 5:
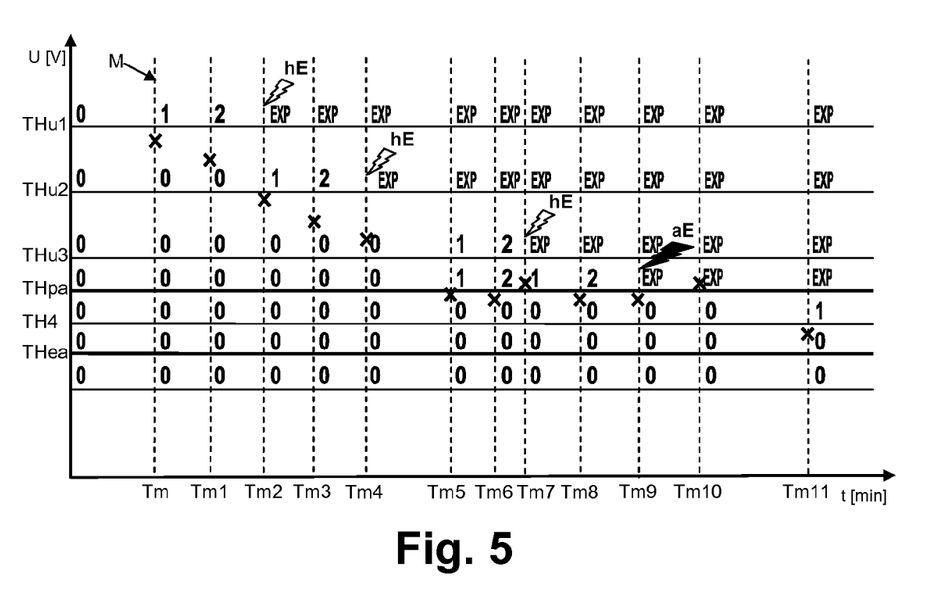
FIG. 5 illustrates a graph illustrating an example of comparing a measured voltage to different threshold values for determining whether an alarm needs to be generated according to an embodiment of the present disclosure.
Figure 6:
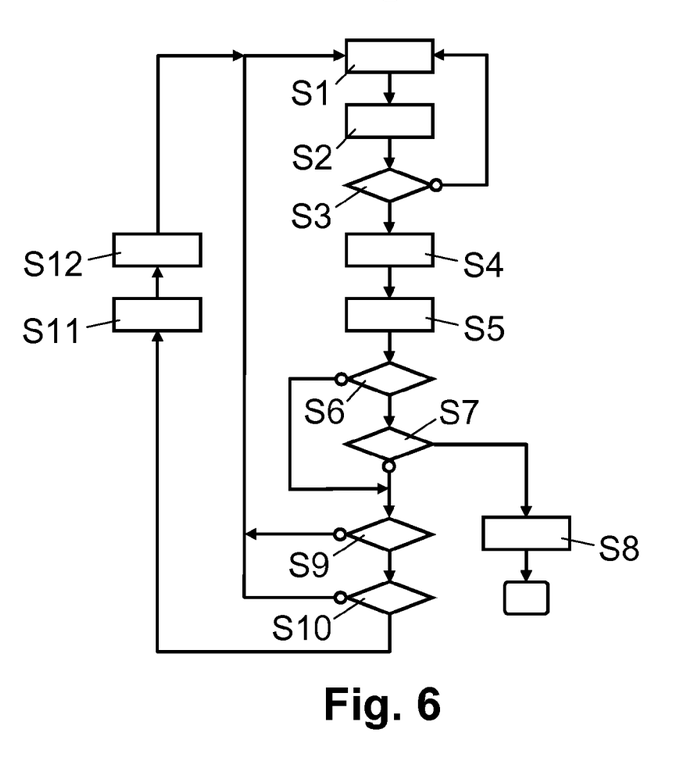
FIG. 6 illustrates a flow diagram illustrating an exemplary sequence of steps for monitoring a replaceable energy storage of a medical device according to an embodiment of the present disclosure.

In the following paragraphs, described with reference to FIGS. 4-6 are possible sequences of steps performed by the functional modules of the monitoring system 12 or device control unit 100, respectively, for monitoring the voltage or charge of the energy storage 10.

As illustrated in FIG. 6, in step S1, the monitoring system 12 can receive from the control units 13, 13', 13" data about energy consuming activities or energy consumed by functional units 14, 14', 14". Depending on the embodiment, the data can be transferred from the control units 13, 13', 13" to the monitoring system 12 upon request (pull mode) or unsolicited (push mode). Alternatively, the control units 13, 13', 13" can write the data with a time stamp into a data store, and the monitoring system 12 can periodically retrieve updated data from that data store. Specifically, depending on the type of functional unit 14, 14', 14", the control units 13, 13', 13" can report to the monitoring system 12 specific values of energy consumed by the respective functional unit 14, 14', 14", for example, in charge units of µAs, or simply an activity by the respective functional unit 14, 14', 14", for example, "on" or "off", which can be used by the monitoring system 12 to calculate corresponding amount of energy consumed by the respective functional unit 14, 14', 14" based on a known current that can be drawn by these units. For example, in FIG. 4, reference numeral A1 refers to an activity of three consecutive power events PE within the time interval [2,3], for example three consecutive movements by the pump motor. For each of these power events PE, the respective control unit 13, 13', 13" can report to the monitoring system 12 a corresponding value of consumed energy or charge. Reference numeral A2, refers to an ongoing activity by a respective functional unit 14, 14', 14" which can be turned on in time interval [4,5] and can be turned off in time interval [8,9]. Accordingly, the functional unit 14, 14', 14" related to the ongoing activity A2 can be registered (deregistered) by the monitoring system 12 as an active (inactive) consumer upon reporting by the associated control unit 13, 13', 13".

In step S2, the monitoring system 12 can determine the current value of energy EC consumed by the functional units 14, 14', 14" based on the data received from the control units 13, 13', 13". Specifically, the monitoring system 12 can calculate an aggregated value of the energy consumed by the functional units 14, 14', 14" by adding up amounts of energy, in accordance with the data provided by the control units 13, 13', 13" about the energy consuming activities performed by the functional units 14, 14', 14" or about the energy consumed by the functional units 14, 14', 14", respectively. The current value of consumed energy EC can be calculated as a running total by adding immediately upon receipt specific amounts of consumed energy, and by adding periodically registered energy consumers, for example, in an 1/s update interval. For that purpose, the monitoring system 12, or device control unit 100, respectively, can comprise data, for example, a table of defined energy consumed by the various functional units 14, 14', 14" and their associated activities, as illustrated in exemplary Table 1. The monitoring system 12 can store the current value of consumed energy EC in data store 122.

TABLE 1

| Activity | Calculation | Value (example) |
| --- | --- | --- |
| Basic energy requirement | Basic energy or charge consumption × time | 300 µA |
| Motor activity | Charge per motor activity | 300 µAs |
| Error, maintenance, warning, reminder handler | Power consumption × time | 35000 µA |
| Menu activity | Power consumption × time | 110000 µA |
| Display in dark state (backlight) | Power consumption × time | 40000 µA |
| RF standby current | Power consumption × time | 600 µA |
| Illumination of ampoule | Power consumption × time | 5000 µA |
| Rewind operation | Power consumption × time | 95000 µA |

As shown in FIG. 4, a value corresponding to the basic power requirement Eb of the device 1 can be added periodically to the current value of consumed energy EC. In FIG. 4, the value of consumed energy related to the power events PE of activities A1 can be added to the current value of consumed energy EC upon reporting by the control unit 13, 13', 13". In an alternative embodiment, the value of consumed energy related to the power events PE can be tracked by incrementing intermediate counters assigned to the power events PE of activities A1. The current value of these intermediate counters can be added periodically with the update interval to the current value of consumed energy EC (in FIG. 4, for example, at time t=3 sec). In addition, the monitoring system 12 can add periodically with the update interval consumed energy corresponding to the registered consumer(s) associated with the ongoing activity A2 (in the FIG. 4, for example, at times t=5, 6, 7, and 8 sec).

In step S3, the monitoring system 12 can check whether the current value of consumed energy EC stored in data store 122 exceeds a defined current energy threshold value THe1 (or THe2) stored in data store 121. If the energy threshold value THe1 (or THe2) is not exceeded, the monitoring system 12 can continue processing in step S1. Otherwise, the monitoring system 12 can determine that it is time Tm for a measurement M of the voltage of the energy store 10 and can continue processing in step S4.

In step S4, the monitoring system 12 can reset in data store 122 the current value of consumed energy EC by (subtracting) the current energy threshold value THe1 stored in data store 121. For example, in FIG. 4, in time interval [11, 12], the reset value of consumed energy EC can be kept above zero only by the basic energy requirement value Eb which can be added for the respective time interval.

In step S5, the monitoring system 12 can trigger the measuring system 11 to measure the voltage of the energy store 10, as indicated in FIG. 4 by trigger event Tg. The measuring module 11 can respond by performing the requested voltage measurement and returning to the monitoring system 12 the current value of the voltage of the energy store 11.

In step S6, the monitoring system 12 can compare the current value of the voltage to an end alarm threshold THea which indicates a voltage or charge level of the energy storage 11 that is insufficient for continued powering of the device 1 in a safe and reliable fashion. If the current voltage of the energy storage 10 is below the end alarm threshold THea, the monitoring system 12 can increment the counter 123b assigned to the voltage threshold value 123a corresponding to the end alarm threshold THea, and can continue processing in step S7. Otherwise, the monitoring system 12 can decrement the respective counter 123b, if it is not set to zero, and can continue processing in step S9.

In step S7, the monitoring system 12 can check whether the counter 123b associated with the end alarm threshold THea exceeds a defined counter threshold value. In other words, the monitoring system 12 can check whether the voltage of the energy storage 10 has been repeatedly below the end alarm threshold THea for more than a defined number of times, for example, more than two times. If that is the case, in step S8, the monitoring system 12 can generate an end alarm which indicates a low energy level of the energy storage 10 that is insufficient for supporting further operation of the device 1. Furthermore, the end alarm can be stored as an alarm event, including the time, and the respective counter can be set to an expired state EXP and can no longer be maintained. Otherwise, if the counter 123b associated with the end alarm threshold THea does not exceed the defined counter threshold value, the monitoring system 12 can continue processing in step S9.

In step S9, the monitoring system 12 can compare the current value of the voltage to a preliminary alarm threshold THpa which indicates a low voltage or charge level which is sufficient for continued powering of the device 1 for a relatively short period of time. If the current voltage of the energy storage 10 is below the preliminary alarm threshold THpa, the monitoring system 12 can increment the counter 123b assigned to the voltage threshold value 123a corresponding to the preliminary alarm threshold THpa, and can continue processing in step S10. In FIG. 5, at measurement time Tm5, the voltage of the energy storage 10, marked by an "x", is below the preliminary alarm threshold THpa and, thus, the respective counter can be incremented to "1". Otherwise, if the voltage is not below the preliminary alarm threshold THpa, the monitoring system 12 can decrement the respective counter 123b, if it is not set to zero, and can continue processing in step S1. For example, in FIG. 5, at measurement time Tm7, the voltage of the energy storage 10 has risen above the preliminary alarm threshold THpa and, thus, the respective counter can be decremented from "2", set at measurement time Tm6, to "1".

In step S10, the monitoring system 12 can check whether the counter 123b associated with the preliminary alarm threshold THpa exceeds a defined counter threshold value. In other words, the monitoring system 12 can check whether the voltage of the energy storage 10 has been repeatedly below the preliminary alarm threshold THpa for more than a defined number of times, for example, more than two times. If that is the case, in step S11, the monitoring system 12 can generate a preliminary alarm which can indicate to the user that the energy storage 10 should be replaced because of a low energy level which may support further operation of the device 1 only for a relatively short period of time. Furthermore, the preliminary alarm can be stored as an alarm event, including the time, and the respective counter can be set to an expired state EXP and can no longer be maintained. In FIG. 5, at measurement time Tm9, the voltage of the energy storage 10 is below the preliminary alarm threshold THpa and the incremented value of the respective counter exceeds the counter value of two so that the counter can be set to the expired state EXP and a preliminary alarm aE can be generated. Otherwise, if the counter 123b associated with the end alarm threshold THpa does not exceed the defined counter threshold value, the monitoring system 12 can continue processing in step S1.

In step S12, the monitoring system 12 can adjust the current energy threshold value stored in data store 121 to a lower energy threshold value THe2. Consequently, when the energy storage 10 has a low energy level, its voltage can be measured more frequently, i.e. at lower energy consumption EC.

In one embodiment, for keeping a log of the discharge behavior and performance of the energy storage 10, the monitoring system 12 can compare the current value of the voltage not only to the preliminary and end alarm thresholds THpa, THea, but also to other voltage thresholds THu1, THu2, THu3, THu4. Accordingly, the monitoring system 12 can maintain additional counters 123b assigned to each of the voltage threshold values 123a corresponding to these voltage thresholds THu1, THu2, THu3, THu4, incrementing a counter when the current voltage of the energy storage 10 is below the voltage threshold THu1, THu2, THu3, THu4, and decrementing a previously incremented counter when the current voltage of the energy storage 10 raises again to a level above the threshold THu1, THu2, THu3, THu4. If a counter associated with a voltage threshold THu1, THu2, THu3, THu4 exceeds a defined counter threshold value, a respective history or log event hE can be generated and stored and the counter can be set to an expired state EXP and can no longer be maintained.

In FIG. 5, voltage values measured at different times of measurement Tm, Tm1, Tm2, Tm3, Tm4, Tm5, Tm6, Tm7, Tm8, Tm9, Tm10, Tm11 are indicated by an "x". In FIG. 5, at time Tm, the voltage of the energy storage 10 is below the voltage threshold THu1 and the respective counter is incremented to "1". Subsequently, at time Tm1, the voltage is again below the voltage threshold THu1 and the respective counter is incremented to "2". In the measurement at time Tm2 the voltage of the energy storage 10 is found to be below the voltage thresholds THu1 and THu2. Accordingly, the counter associated with voltage threshold THu2 can be incremented, and, because the incremented value of the counter associated with voltage threshold THu1 exceeds the counter threshold of two, a history or log event hE can be generated for the voltage threshold THu1, including the time of measurement Tm2 and the respective counter can be set to an expired state EXP. Correspondingly, a history or log event hE can be generated for the voltage threshold THu2 as the voltage of the energy storage 10 is below the voltage threshold THu2 at the measurement times Tm3 and Tm4. An example of a history/event log corresponding to the example of FIG. 5 is shown in Table 2.

TABLE 2

History/Event Log
(for given type of device 1 and given type of energy storage 10)

| Event | Threshold | Voltage | Time |
|---|---|---|---|
| Historic event hE | Voltage threshold THu1 | U2 | Tm2 |
| Historic event hE | Voltage threshold THu2 | U4 | Tm4 |

TABLE 2-continued

History/Event Log
(for given type of device 1 and given type of energy storage 10)

| Event | Threshold | Voltage | Time |
|---|---|---|---|
| Historic event hE | Voltage threshold THu3 | U7 | Tm7 |
| Preliminary alarm event aE | Preliminary alarm threshold THpa | U9 | TM9 |

In addition to triggering the measurement of the voltage of the energy storage 10 depending on the consumed energy, or a defined change in temperature, the measurement of the voltage may be triggered, in additional embodiments, by other defined events such as start-up of the device, for example, at insertion or replacement of the energy storage 10, or a self-testing operation of the device 1.

It should be noted that, the role of incrementing and decrementing counters may also be reversed. Furthermore, the computer program code has been associated with specific functional modules and the sequence of the steps has been presented in a specific order, one skilled in the art will understand, however, that the computer program code may be structured differently and that the order of at least some of the steps could be altered, without deviating from the scope of the invention.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. An ambulatory infusion device, the ambulatory infusion device comprising:
a replaceable energy storage for electrically powering several functional units of the ambulatory infusion device;
a measuring module to measure a voltage of the replaceable energy storage; and
a monitoring system to determine on an ongoing basis energy consumed by the functional units by adding up amounts of energy based on data provided by control units associated with the functional units, to trigger the measuring module to measure the voltage of the energy storage at a point in time which depends on the energy consumed by the functional units in a time interval preceding the point in time, and to generate an alarm depending on the voltage of the energy storage.

2. The ambulatory infusion device according to claim 1, wherein the functional units comprise at least one functional hardware unit controlled by one of the control units which provide the monitoring system data about energy consuming activities or energy consumed by the hardware unit.

3. The ambulatory infusion device according to claim 2, wherein the monitoring system determines the energy consumed by the functional units based on the data provided by the control units controlling the hardware units.

4. The ambulatory infusion device according to claim 2, wherein the monitoring system compares a current value of energy consumed by the functional units to an energy threshold value, triggers the measuring module to measure the voltage of the energy storage for cases where the current value of consumed energy exceeds the energy threshold value, and resets the current value of energy consumed by the energy threshold value, upon having triggered the measuring module.

5. The ambulatory infusion device according to claim 4, wherein the monitoring system determines the energy threshold value depending on at least one of: a type of energy storage used in the ambulatory infusion device, a current temperature value, a course of the temperature value, the voltage of the energy storage, and a course of the voltage of the energy storage.

6. The ambulatory infusion device according to claim 1, wherein the monitoring system generates a preliminary alarm indicative of a low energy level, sufficient for supporting further operation of the ambulatory infusion device for cases where the voltage of the energy storage meets alarm conditions associated with an upper voltage threshold value, and generates an end alarm indicative of a low energy level, insufficient for supporting further operation of the ambulatory infusion device for cases where the voltage of the energy storage meets alarm conditions associated with a lower voltage threshold value.

7. The ambulatory infusion device according to claim 1, wherein the monitoring system maintains counters for several voltage threshold values, increments a counter value when the voltage of the energy storage falls below the respective voltage threshold value and decrements the counter value when the energy storage subsequently exceeds the respective voltage threshold value again, up to a defined counter threshold value when the energy storage is considered to have fallen definitely below the respective voltage threshold value.

8. The ambulatory infusion device according to claim 7, wherein the monitoring system maintains an event log including for the voltage threshold values in each case a point in time when the energy storage is considered to have fallen definitely below the respective voltage threshold value.

9. A method of monitoring a replaceable energy storage of a medical device which includes several functional units electrically powered by the energy storage, the method comprising:
determining on an ongoing basis energy consumed by the functional units by adding up amounts of energy based on data provided by control units associated with the functional units;
measuring a voltage of the energy storage at a point in time determined based on the energy consumed by the functional units in a time interval preceding the point in time; and
generating an alarm depending on the voltage of the energy storage.

10. The method according to claim 9, further comprises
receiving from the control units data about energy consuming activities or energy consumed by functional hardware units; and
determining the energy consumed by the functional units based on the data about energy consuming activities or consumed energy or charge.

11. The method according to claim 9, further comprises,
comparing a current value of energy consumed by the functional units to an energy threshold value;

measuring the voltage of the energy storage for the case where the current value of consumed energy exceeds the energy threshold value; and resetting the current value of energy consumed by the energy threshold value upon having measured the voltage of the energy storage.

12. The method according to claim 11, further comprises, determining the energy threshold value depending on at least one of: a type of energy storage used in the medical device, a type of battery used as energy storage used in the medical device, a current temperature value, a change in the temperature value, the voltage of the energy storage, and a course of the voltage of the energy storage.

13. The method according to claim 9, further comprises, generating a preliminary alarm indicative of a low energy level, sufficient for supporting further operation of the medical device for cases where the voltage of the energy storage meets alarm conditions associated with an upper voltage threshold value; and generating an end alarm indicative of a low energy level, insufficient for supporting further operation of the medical device for cases where the voltage of the energy storage meets alarm conditions associated with a lower voltage threshold value.

14. The method according to claim 9, further comprises, maintaining counters for several voltage threshold values;

incrementing a counter value when the voltage of the energy storage falls below the respective voltage threshold value; and decrementing the counter value when the energy storage subsequently exceeds the respective voltage threshold value again, up to a defined counter threshold value when the energy storage is considered to have fallen definitely below the respective voltage threshold value.

15. A computer program product comprising a non-transitory computer readable medium having stored thereon computer program code configured to direct a processor of a medical device, which includes a replaceable energy storage for electrically powering several functional units of the medical device, such that the processor:

determines on an ongoing basis energy consumed by the functional units by adding up amounts of energy based on data provided by control units associated with the functional units;

triggers a measuring module of the medical device to measure the voltage of the energy storage at a point in time determined based on the energy consumed by the functional units in a time interval preceding the point in time; and generates an alarm depending on the voltage of the energy storage.

* * * * *